United States Patent [19]

Tsuchida et al.

[11] Patent Number: 5,188,947
[45] Date of Patent: Feb. 23, 1993

[54] PROCESS AND MICROORGANISM FOR PRODUCING L-ORNITHINE BY CORYNEBACTERIUM, BREVIBACTERIUM, OR ATHROBACTER

[75] Inventors: Takayasu Tsuchida; Haruo Uchibori; Yoshitaka Nishimoto, all of Kawasaki, Japan

[73] Assignee: Ajinomoto Co., Inc., Tokyo, Japan

[21] Appl. No.: 512,108

[22] Filed: Apr. 20, 1990

[30] Foreign Application Priority Data

Apr. 20, 1989 [JP] Japan .................................. 1-101011

[51] Int. Cl.$^5$ ............................................ C12P 13/10
[52] U.S. Cl. .................................. 435/114; 435/252.1; 435/830; 435/843; 435/840
[58] Field of Search ...................... 435/114, 252.1, 830, 435/840, 843

[56] References Cited

U.S. PATENT DOCUMENTS 2,988,489  6/1961  Kinoshita et al. .................... 435/114
3,532,600 10/1970  Okumura et al. .................... 435/114

FOREIGN PATENT DOCUMENTS 0016696  1/1982  Japan .
1140827  1/1969  United Kingdom .
1178005  1/1970  United Kingdom .

OTHER PUBLICATIONS

Patent Abstracts of Japan, unexamined applications, C field, vol. 7, No. 7, Jan. 12, 1983, p. 166 C 144, Kokai-No. 57-166 988.
Patent Abstracts of Japan, unexamined applications, C field, vol. 10, No. 310, Oct. 22, 1986, p. 37 C 379, Kokai-No. 61-119 194.

Primary Examiner—Douglas W. Robinson
Assistant Examiner—Marian C. Knode
Attorney, Agent, or Firm—Oblon, Spivak, McClelland, Maier & Neustadt

[57] ABSTRACT

A process for producing L-ornithine by fermentation which comprises culturing a L-ornithine-producing microorganism is disclosed. The microorganism used belongs to the genus Brevibacterium, Corynebacterium, or Arthrobacter, has auxotrophy for arginine and/or citrulline, and has resistance to microphenolic acid and/or ornithinol.

7 Claims, No Drawings

PROCESS AND MICROORGANISM FOR PRODUCING L-ORNITHINE BY CORYNEBACTERIUM, BREVIBACTERIUM, OR ATHROBACTER

BACKGROUND OF THE INVENTION

1. Field of the Invention

The present invention relates to processes and microorganisms for producing L-ornithine by fermentation.

2. Discussion of the Background

L-Ornithine is an important component of drugs for stimulating liver functions, total amino acid preparations, etc.

Some microorganisms belonging to the genus Brevibacterium or to the genus Corynebacterium are known to produce L-ornithine. These include citrulline or arginine auxotroph which belong to the genus Brevibacterium (Japanese Patent Publication No. 43-8712), citrulline or arginine auxotroph which belong to the genus Bacillus (Japanese Patent Publication No. 43-10996), citrulline or arginine analogues which belong to the genus Arthrobacter (Japanese Patent Publication No. 44-24303), variants having resistance to arginine analogues belonging to the genus Corynebacterium (Japanese Patent Application Laid-Open No. 53-24096), or variants which belong to the genus Corynebacterium having resistance to 2-thiazolealanine, sulfaguanidine or 2-fluoropyruvic acid (Japanese Patent Application Laid-Open No. 61-119194)

To reduce the costs of producing L-ornithine however, in particular industrial-scale production costs, there is a current need for bacterial strains providing improved fermentation yields of this material.

SUMMARY OF THE INVENTION

The present invention provides such bacterial strains which can be advantageously used in the large scale, e.g., industrial, production of L-ornithine. As a result of investigations directed at improving the ability of known microorganisms belonging to the genus Brevibacterium, Corynebacterium, or Arthrobacter, to produce L-ornithine and finding bacterial strains further providing improved L-ornithine fermentation yields, the inventors have discovered bacterial strains capable of producing L-ornithine in a higher yield than conventional orthinine-producing strains. Such bacterial strains of the invention are strains to which resistance to mycophenolic acid and/or ornithinol has been imparted.

BRIEF DESCRIPTION OF THE PREFERRED EMBODIMENTS

The present invention thus provides a process for producing L-ornithine which comprises culturing under known conditions an L-ornithine-producing microorganism belonging to the genus Brevibacterium, Corynebacterium, or Arthrobacter, having auxotrophy for arginine or citrulline and having resistance to mycophenolic acid and/or ornithinol in a liquid medium, and collecting L-ornithine produced and accumulated in the medium.

The microorganisms used in the present invention are variants belonging to the genus Brevibacterium. Corynebacterium, or Arthrobacter. having resistance to mycophenolic acid and/or ornithinol and which are capable of producing L-ornithine. The resistance may be either mycophenolic acid resistance or ornithinol resistance. Or the microorganisms may also have both resistances.

To obtain the variants of the present invention, L-ornithine productivity may first be imparted to one of the wild strains described below, and then mycophenolic acid resistance or ornithinol resistance is imparted. Alternatively, mycophenolic acid resistance or ornithinol resistance may first be imparted to one of the wild strains, and then L-ornithine productivity such as arginine auxotrophy or citrulline auxotrophy is then imparted.

Wild strains which can be parent strains from which the variants of the present invention are obtained include bacteria belonging to the genus Brevibacterium, Corynebacterium, or Arthrobacter. Coryneform capable of producing L-glutamic acid are preferred. These are exemplified by the following bacteria.

| Microorganism | Identification No. |
| --- | --- |
| Brevibacterium divaricatum | ATCC 14020 |
| Brevibacterium flavum | ATCC 14067 |
| Brevibacterium lactofermentum | ATCC 13869 |
| Brevibacterium saccharolyticum | ATCC 14066 |
| Corynebacterium acetoacidophilum | ATCC 13870 |
| Corynebacterium glutamicum | ATCC 13032 |
| Arthrobacter protophormiae | ATCC 17775 |

The above organism are on deposit with the American Type Culture Collection (ATCC), 12301 Parklawn Drive, Rockville, Maryland 20852 (USA).

To induce the variants of the present invention from these parent strains by mutation, conventional methods for mutation may be used. These comprise contacting the parent strain with N-methyl-N'-nitro-N-nitrosoguanidine, etc.

A specific method for mutation of the variant of the present invention and a relationship between the concentration of mycophenolic acid or ornithinol and growth of the strain are provided below for purposes of illustrating the invention.

Method for inducing mutation:

*Arthrobacter citreus* bacterial cells AJ 12441 (FERM BP-2341) having arginine auxotrophy, which had been grown in a bouillon agar slant at 30° C. for 24 hours, were suspended in M/30 phosphate buffer solution. To the cell suspension was added 100 $\mu$g/ml of N-methyl-N'-ntro-N-nitrosoguanidine and the mixture was allowed to sit at 30° C. for 30 minutes. The cells were then collected. After thoroughly washing with M/30 phosphate buffer solution, the cells were inoculated on a medium having the composition set forth below and cultured at 31.5° C. for 5 days. Among the bacterial strins grown on the medium, the large colonies were recovered. Most o the recovered strains had a high L-orithine productivity.

| Composition of the Medium (pH 7.0) | |
| --- | --- |
| Component | Content |
| Glucose | 1 g/dl |
| Urea | 0.2 g/dl |
| KH$_2$PO$_4$ | 0.1 g/dl |
| MgSO$_4$.7H$_2$O | 0.1 g/dl |
| FeSO$_4$.7H$_2$O | 0.002 g/dl |
| MnSO$_4$.7H$_2$O | 0.002 g/dl |
| Biotin | 100 $\mu$g/l |
| Thiamine hydrochloride | 100 $\mu$g/l |
| L-Arginine | 15 mg/dl |
| Mycophenolic acid | 0.1 g/dl |
| Agar | 2.0 g/dl |

-continued

| Composition of the Medium (pH 7.0) | |
|---|---|
| Component | Content |
| pH | 7.2 |

From the strains grown on the agar medium, the *Arthrobacter citreus* AJ 12442 (FERM BP-2342; arginine auxotrophy or citrulline auxotrophy and mycophenolic acid resistance) obtained displayed a high ability to produce L-ornithine.

Ornithinol-resistant *Brevibacterium lactofermentum* cells AJ 12444 (FERM BP-2344) were bred from *Brevibacterium lactofermentum* AJ 12443 (FERM BP-2343; arginine or citrulline auxotrophy) in a manner similar to the method described above except that the L-arginine and mycophenolic acid components used in the medium described above were replaced with chemicals required for their production or for imparting resistance to them. *Corynebacterium qlutamicum* AJ 12445 (FERM BP-2345; arginine or citrulline auxotrophy and vitamin P resistance, mycophenolic acid resistance and ornithinol resistance) cells were collected from *Corynebacterium olutamicum* AJ 11589 (FERM P-5644; arginine or citrulline auxotrophy and vitamin P resistance) by the method of breeding twice. The mycophenolic acid or ornithinol resistance of the thus obtained variants was compared with that of the parent strains.

Onto a medium composed of 0.5 g/dl of glucose, 0.15 g/dl of urea, 0.15 g/dl of ammonium sulfate, 0.3 g/dl of $KH_2PO_4$, 0.1 g/dl of $K_2HPO_4$, 0.01 g/dl of $MgSO_4.7H_2O$, 0.1 mg/dl of $CaCl_2.2H_2O$, 100 $\mu g/l$ of biotin, 100 $\mu g/l$ of thiamine hydrochloride, 0.002 g/dl of $FeSO_4.7H_2O$, 0.002 g/dl of $MnSO_4.7H_2O$, 15 mg/dl of L-arginine and mycophenolic acid or ornithinol in the amounts shown in the table and adjusted to pH 7.0, there was inoculated a suspension of the cells in a sterile water, which cells had been obtained by culturing in natural medium (1 g/dl of polypeptone, 1 g/dl of yeast extract and 0.5 g/dl of NaCl, pH 7.0) slant at 31.5° C. for 24 hours. After shake culture in a test tube for 24 hours, the growth degree was determined in terms of media turbidity.

Media used for culturing such variants may be conventional media containing carbon sources, nitrogen sources, inorganic ions, substances satisfying the auxotrophy described above and, if necessary, other organic trace nutrients including vitamin, etc. As carbon sources one preferably uses carbohydrates such as glucose, sucrose, etc., organic acids such as acetic acid, etc. As nitrogen sources one preferably usedsammonia water, ammonia gas, ammonium salts, etc. As inorganic ions, potassium ions, sodium ions, magnesium ions, phosphate ions and the like may be appropriately added to media, depending upon necessity.

Incubation is carried out under aerobic conditions. Preferably the incubation is carried out using a pH for the medium of from 4 to 8, at a temperature of from 25° C. to 37° C. When the bacterial cells of the invention are cultured for 1 to 7 days, remarkable amounts of L-ornithine are produced and accumulated in the medium.

To collect L-ornithine from the culture solution, conventional method such as a method using ion exchange resin, etc. can be used.

Having generally described this invention, a further understanding can be obtained by reference to certain specific examples which are provided herein for purposes of illustration only and are not intended to be limiting.

EXAMPLE

Media containing 10 g/dl of glucose, 7 g/dl of $(NH_4)_2SO_4$, 0.15 g/dl of $KH_2PO_4$, 0.04 g/dl of $MgSO_4.7H_2O$, 1 mg/dl of $FeSO_4.7H_2O$, 1 mg/dl of $MnSO_4.4H_2O$, 100 $\mu g/l$ of thiamine hydrochloride, 100 $\mu g/l$ of biotin, 60 mg of soybean protein acid hydrolysate (calculated as total nitrogen) and 15 mg/dl of L-arginine and 5 g/dl of calcium carbonate (independently sterilized) was adjusted to pH 7.2 and 25 ml of the media was charged into a 500 ml flask equipped with a shoulder followed by sterilization with heating. One platinum loop of the strain shown in Table 2 was inoculated on the medium and shaken for 4 days while keeping at 31.5° C. L-Ornithine was produced and accumulated in the culture solution of each strain in the amount shown in Table 2.

TABLE 1

| | Concentration of Mycophenolic Acid (%) | | | | | Concentration of Ornithinol (%) | | | | |
|---|---|---|---|---|---|---|---|---|---|---|
| | 0 | 0.05 | 0.1 | 0.2 | 0.3 | 0 | 0.05 | 0.1 | 0.2 | 0.3 |
| *Arthrobacter citreus* AJ 12441 (FERM BP-2341) | 0.95 | 0.45 | 0 | 0 | 0 | | | | | |
| *Arthrobacter citreus* AJ 12442 (FERM BP-2342) | 0.96 | 0.90 | 0.90 | 0.85 | 0.70 | | | | | |
| *Brevibacterium lactofermentum* AJ 12443 (FERM BP-2343) | | | | | | 0.95 | 0.90 | 0.50 | 0.10 | 0 |
| *Brevibacterium lactofermentum* AJ 12444 (FERM BP-2344) | | | | | | 0.95 | 0.95 | 0.90 | 0.85 | 0.85 |
| *Corynebacterium glutamicum* AJ 11589 (FERM BP-5644) | 0.90 | 0.40 | 0.10 | 0 | 0 | 0.92 | 0.90 | 0.65 | 0.20 | 0 |
| *Corynebacterium glutamicum* AJ 12445 (FERM BP-2345) | 0.95 | 0.90 | 0.85 | 0.90 | 0.80 | 0.95 | 0.90 | 0.95 | 0.80 | 0.85 |

Other microorganisms belonging to the genus Brevibacterium, Corynebacterium, or Arthrobacter which are used in the process of the present invention obtained using the protocol described above.

TABLE 2

| Strain | Property | Amount of L-Ornithine Accumulated (g/dl) |
|---|---|---|
| Arthrobacter citreus AJ 12441 (FERM BP-2341) | Arg⁻(or Cit⁻) | 3.5 |
| Arthrobacter citreus AJ 12442 (FERM BP-2342) | Arg⁻(or Cit−) × MPAγ | 5.0 |
| Brevibacterium lactofermentum AJ 12443 (FERM BP-2343) | Arg⁻(or Cit⁻) | 4.7 |
| Brevibacterium lactofermentum AJ 12444 (FERM BP-2344) | Arg⁻(or Cit⁻) × ORLγ | 5.5 |
| Corynebacterium glutamicum AJ 11589 (FERM P-5644) | Arg⁻(or Cit⁻) × VPγ | 4.6 |
| Corynebacterium glutamicum AJ 12445 (FERM BP-2345) | Arg⁻(or Cit⁻) × VPγ × MPAγ × ORLγ | 5.3 |

Arg: arginine auxotrophy
Cit: citrulline auxotrophy
MPAγ: mycophenolic acid resistance
ORLγ: ornithinol resistance
VPγ: vitamin P resistance The process of the present invention provides an improved fermentation yield of L-ornithine, thus reducing production costs.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the U.S. is:

1. A process for producing L-ornithine by fermentation, comprising:
   (i) culturing a microorganism selected for the group consisting of *Arthrobacter citreus* FERM BP-2342, *Brevibacterium lactofermentum* FERM BP-2344, and *Corynebacterium glutamicum* FERM BP-2345, in an aqueous nutrient medium containing assimilable source of carbon, nitrogen, and inorganic substances thereby producing L-ornithine; and
   (ii) isolating the L-ornithine produced.

2. The process of claim 1 wherein said microorganism is *Arthrobactyer citreus* FERM BP-2342.

3. The process of claim 2 wherein said microorganism is obtained by mutation of *Arthrobacter citreus* ATCC 17775.

4. The process of claim 1 wherein said microorganism is *Brevibacterium lactofermentum* FERM BP-2344.

5. The process of claim 4 wherein said microorganism is obtained by mutation of *Brevibacterium lactofermentum* ATCC 13869.

6. The process of claim 1 wherein said microorganism is *Corynebacterium glutamicum* FERM BP-2345.

7. The process of claim 6 wherein said microorganism is obtained by mutation of *Corynebacterium glutamicum* ATEC 13032.

* * * * *